United States Patent
Mous

Patent Number: 5,480,392
Date of Patent: Jan. 2, 1996

[54] ANGIOGRAPHY CATHETER

[75] Inventor: Frans Mous, Drachten, Netherlands

[73] Assignee: Cordis Corporation, Miami Lakes, Fla.

[21] Appl. No.: 191,285

[22] Filed: Feb. 3, 1994

[30] Foreign Application Priority Data

Feb. 4, 1993 [NL] Netherlands .............. 9300231

[51] Int. Cl.⁶ .............. A61M 25/00; A61B 6/00
[52] U.S. Cl. .............. 604/280; 128/658
[58] Field of Search .............. 128/656–658; 604/53, 280, 281

[56] References Cited

U.S. PATENT DOCUMENTS

| | | | |
|---|---|---|---|
| 3,938,501 | 2/1976 | Erikson | 128/2 A |
| 4,531,933 | 7/1985 | Norton et al. | 604/281 |
| 4,671,795 | 6/1987 | Mulchin | 604/281 |
| 4,694,838 | 9/1987 | Wijayarthna et al. | 604/281 |
| 4,735,620 | 4/1988 | Ruiz | 604/281 |
| 4,878,495 | 11/1989 | Grayzel | 128/344 |
| 4,958,634 | 9/1990 | Jang | 606/194 |
| 4,961,731 | 10/1990 | Bodicky et al. | 604/281 |
| 4,986,814 | 1/1991 | Burney et al. | 604/281 |
| 5,163,431 | 11/1992 | Griep | 128/658 |
| 5,201,723 | 4/1993 | Quinn | 604/264 |
| 5,221,253 | 6/1993 | Coll | 604/281 |

FOREIGN PATENT DOCUMENTS

| | | |
|---|---|---|
| 0129634 | 1/1985 | European Pat. Off. . |
| 0154403 | 9/1985 | European Pat. Off. . |
| 0453008 | 10/1991 | European Pat. Off. . |
| 2166958 | 5/1986 | United Kingdom . |

*Primary Examiner*—C. Fred Rosenbaum
*Assistant Examiner*—Frank Wilkens, III
*Attorney, Agent, or Firm*—Thomas R. Vigil

[57] ABSTRACT

The invention relates to an angiography catheter comprising a hose-like body with at least one lumen debouching at the distal end in an end opening, wherein the distal end has a permanent curvature and a number of openings is arranged in the wall. At least some of the openings are herein arranged in the curvature in a side of the wall remote from the end opening. The angiography catheter can be of the so-called "pigtail" type, with a circular curvature through substantially 360°, wherein openings are arranged in the first 180° of the curvature in the outward facing portion of the wall.

4 Claims, 1 Drawing Sheet

ANGIOGRAPHY CATHETER

BACKGROUND OF THE INVENTION

1. Field of the Invention

The invention relates to an angiography catheter comprising a hose-like body with at least one lumen debouching in an end opening at the distal end. The distal end has a permanent curvature and a number of openings is arranged in the wall of the catheter.

2. Description of the Related Art Including Information Disclosed Under 37 CFR §1.97–1.99

Such a catheter is, for example, a diagnostic cardiac catheter which is guided via a blood vessel into the heart. A contrast liquid can be introduced via the lumen so that the contours of, for example, a ventricle of the heart of a patient can be made visible on an X-ray screen in a catheter laboratory. In accordance with the area of the blood vessel system of the patient to be examined, a catheter is used with a specific curvature, which curvature is designed such that the distal end of the catheter will assume a stable position in the intended area.

With known angiography catheters of this type, the curvature can deform quite considerably during injection of the contrast liquid as a result of the reaction forces of the contrast liquid flowing in the curvature and spurting outward from the end opening. This can endanger the stable position of the end portion of the catheter.

The invention now has for its object to improve a catheter of the type described in the preamble such that it also has a stable position during injection of the contrast liquid.

This objective is achieved with an angiography catheter, as characterized in claim 1. Due to the openings arranged in the curvature in a side of the wall remote from the end opening, a quantity of liquid is discharged and the reaction forces resulting from the remaining liquid become accordingly smaller. The pressure in the curvature is thereby also lower whereby the "uncurling", as a result of a Bourdon spring effect, is likewise reduced. Moreover, a reaction force is herein generated which attempts to bend the catheter in a direction opposite to that in which the catheter is bent by the reaction force of the liquid coming out of the end opening. These effects largely cancel each other out so that during injection of the contrast liquid, even if this takes place at high pressure a very limited deformation, at most, of the permanent curvature of the catheter occurs. The angiographic examination can hereby take place more rapidly and accurately.

The invention can be applied particularly well with an angiography catheter of the so-called "pigtail" type. The curvature herein is a circular curvature through practically 360°. In the known "pigtail" catheter, the curvature is bent outward by the reaction force of the liquid spurting out from the end opening, whereby the desired shape of the curvature is disturbed and the direction in which the contrast liquid spurts out is moreover considerably altered. With the catheter according to the invention of the type, openings are arranged in the first 180° of the curvature in the outward facing portion of the wall. These openings drain off a portion of the liquid, whereby the forces in and on the curvature become smaller because the quantity of liquid and the pressure thereof in the curvature decrease. The liquid flowing outward through the openings causes a reaction force which results in strengthening of the curvature of the catheter and, thus, counteracts the "uncurling".

The placing of the openings in the manner according to the invention moreover has the advantage that contrast liquid is better directed towards the apex of the heart ventricle under examination, so that the whole action of the catheter is improved.

The openings arranged in the curvature are preferably additional to the usual openings in the portion of the basic body lying in advance of the curvature. The number of openings in the catheter, according to the invention, is thus larger than in a catheter according to the prior art, so that a more uniform egress of contrast liquid over a larger area is achieved. This moreover achieves that the total quantity of liquid coming out of the end opening is smaller and the pressure of the jet coming out of the end opening of the wall of the heart ventricle toward which this jet is directed during the examination, can decrease greatly. Heart arrhythmia occurring with catheters of this type, according to the prior art, are hereby avoided.

DESCRIPTION OF THE DRAWINGS

The invention will be further elucidated in the following description with reference to the embodiments shown in the Figures.

For elucidation of the principle of the invention FIG. 1 and FIG. 2 show next to each other, an angiography catheter of the "pigtail" type according to the prior art (FIG. 1) and according to the invention (FIG. 2).

The catheter 1 according to the prior art shown in FIG. 1 has, in the usual manner, a basic body 6 with a lumen. In FIG. 1 only the distal end is drawn which, as shown here, has a circular curvature 2 through slightly less than 360°. The end of the lumen debouches into an end opening 3. Arranged in the portion of the basic body 6 lying in advance of the curvature 2 is a number of openings 5 which connect the lumen to the environment.

Figure 1:
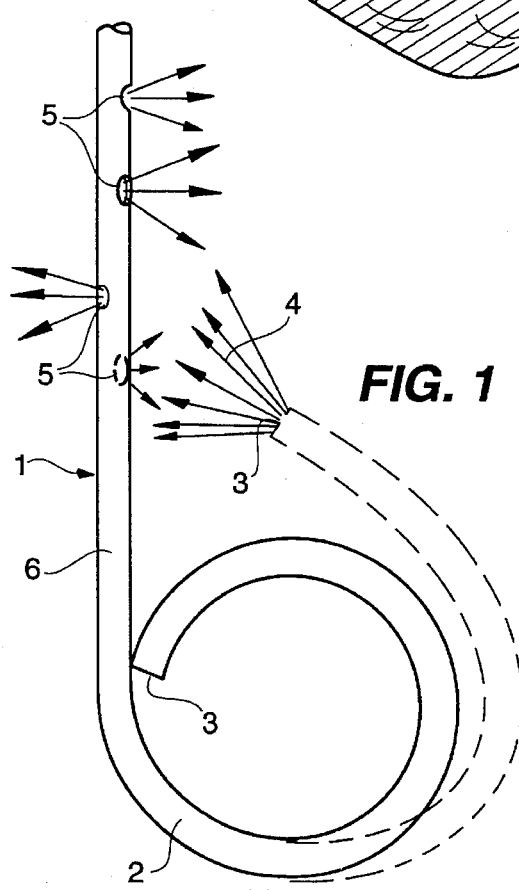
FIG. 1 shows an angiography catheter of the "pigtail" type, according to the prior art.

During use a contrast liquid is injected into the proximal end of the catheter, which liquid comes out at the distal end shown in FIG. 1 through the end opening 3 and the openings 5. The jet 4 coming out of the end opening 3 causes a reaction force on the curvature 2 which results in the "unrolling" of curvature 2. This situation is indicated with dashed lines. During the examination the catheter thus moves as a result of this unrolling effect so that the position thereof is not stable.

Figure 2:
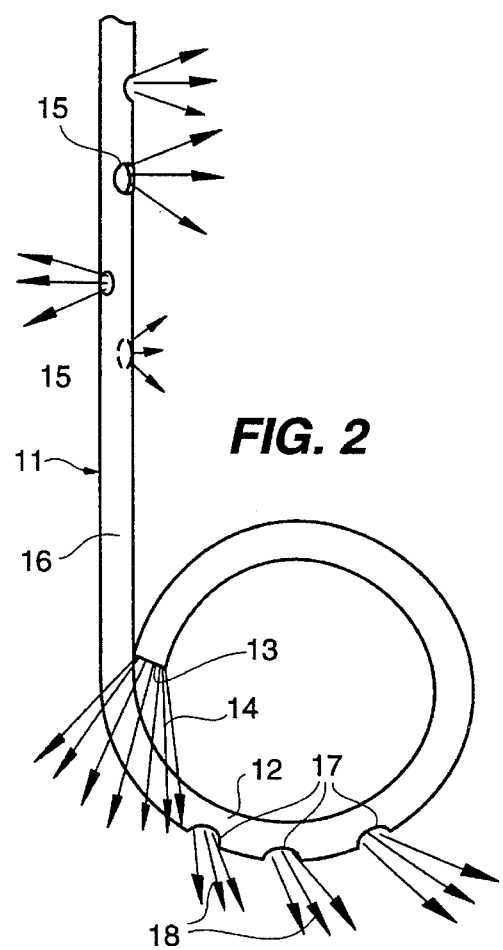
FIG. 2 shows a view corresponding with FIG. 1 of an angiography catheter of the "pigtail" type, according to the invention.

The catheter 11 according to the invention shown in FIG. 2 likewise comprises a basic body 16 with a curvature 12 on the end thereof which is substantially a circular curvature through 360°. Here the lumen also forms an end opening 13 out of which comes a jet 14 of contrast liquid during use.

As shown in FIG. 2, in the first 180° of the curvature, taken from the basic body, openings 17 are arranged in the side of the wall facing away from the end opening 13, that is, in the outward facing portion of the wall. During use of the catheter, jets 18 of contrast liquid egress through these openings 17. These jets 18 cause a reaction force which attempts to enhance the curvature 12 and thus acts counter to the reaction force caused by the jet 14. The effect is that the curvature 14 deforms to a limited degree at most, whereby a considerably more stable position of the curvature is obtained.

The catheter shown in FIG. 2 is a preferred embodiment wherein the openings 17 are additional to the openings 15 arranged in the conventional manner in the portion of the basic body 16 lying in advance of the curvature. These openings 15 correspond to the openings 5 in the catheter 1 according to the prior art.

In this preferred embodiment, the number of openings in the distal end of the catheter is thus increased, so that the jet 14 finally coming out of the end opening 13 is considerably less powerful than according to the prior art. This also reduces the "unrolling" effect of the jet 14.

Figure 3:
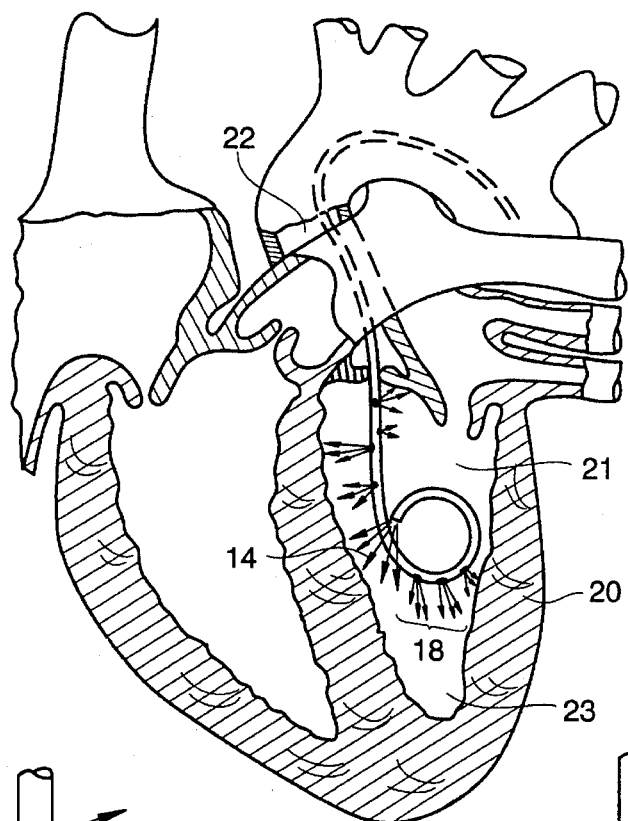
FIG. 3 shows the catheter of FIG. 2 during use.

As FIG. 3 shows, the jet 14 is usually oriented to the wall of the heart ventricle 21 during the examination of the heart 20 of a patient. Since in the preferred embodiment of the invention the strength of jet 14 is reduced, the irritation of the wall of the heart ventricle 21 is limited, so that the heart rhythm is not disturbed or much less so.

FIG. 3 also shows that the catheter of the "pigtail" type described here is carried via the aorta 22 into the ventricle 21. Due to the specific shape of the curvature, the end portion of the catheter remains lying stably in the ventricle 21 in the manner shown. During injection of the contrast liquid the catheter, according to the invention, also retains its position.

An additional advantage of the openings 17 arranged in the curvature is that the jets 18 of contrast liquid coming out therethrough penetrate well into the apex 23 of the heart ventricle 21 so that on an X-ray screen a clear image of the contours of the ventricle 21 can be obtained.

Although the invention can be applied particularly favorably in the case of the described angiography catheter of the "pigtail" type, the invention is not limited to use with this type of catheter. In all angiography catheters with a curved end, openings can be arranged according to the invention in the wall of the curvature, in a side of the wall facing away from the end opening, in order to obtain the described effect of counteracting the deformation of the curvature by the jet coming out of the end opening.

I claim:

1. An angiography catheter of the "pigtail" type comprising a tubular body having a generally cylindrical wall, a proximal end, a main portion, a distal end portion, a distal end and at least one lumen debouching at the distal end in an end opening, said distal end portion having a permanent, at least partially generally circular curvature that lies in a plane that also contains a distal portion of said main portion and having a number of openings arranged only in a portion of a wall facing outwardly of said generally circular curvature in said distal end portion and in said plane, said openings being arranged in the curvature in a side of said wall of said distal end portion remote from said end opening and facing in a direction in said plane containing said at least partially generally circular curvature and said distal portion of said main portion, whereby fluid exiting said openings in side of said wall of said distal end portion having said curvature will reduce, if not eliminate, any force of said fluid on said distal end portion having said curvature that tends to "uncurl" said distal end portion having said curvature.

2. An angiography catheter of the "pigtail" type with a circular curvature through substantially 360° of a distal end portion of said catheter, said catheter comprising a tubular body having a generally cylindrical wall, a proximal end, a main portion, said distal end portion, a distal end and at least one lumen debouching at the distal end in an end opening, said distal end portion having a permanent curvature and having a number of openings arranged in said wall in said distal end portion, at least some of said openings being arranged in the first 180° of the curvature in an outward facing portion of a side wall of said distal end portion remote from said end opening and facing in a direction whereby fluid exiting said openings in said side wall of said distal end portion having said curvature will reduce, if not eliminate any force of said fluid on said distal end portion having said curvature that tends to "uncurl" said distal end portion having said curvature.

3. An angiography catheter of the "pigtail" type with a circular curvature through substantially 360° of a distal end portion of said catheter, said catheter comprising a tubular body having a generally cylindrical wall, a proximal end, main portion, said distal end portion, a distal end and at least one lumen debouching at the distal end in an end opening, said distal end portion having permanent curvature and having a number of openings arranged in said wall in said distal end portion at least some of said openings being arranged in the first 90° of the curvature in the outward facing portion of a side wall of said distal end portion remote from said end opening and facing in a direction whereby fluid exiting said openings in said side wall of said distal end portion having said curvature will reduce, if not eliminate, any force of said fluid on said distal end portion having said curvature that tends to "uncurl" said distal end portion having said curvature.

4. The angiography catheter as claimed in 2, wherein said openings arranged in the curvature of said distal end portion are additional to openings arranged in a known per se manner in said main portion of said tubular body positioned in advance of the curvature.

* * * * *

UNITED STATES PATENT AND TRADEMARK OFFICE
CERTIFICATE OF CORRECTION

PATENT NO. : 5,480,392

DATED : January 2, 1996

INVENTOR(S) : Frans Mous

Page 1 of 3

It is certified that error appears in the above-indentified patent and that said Letters Patent is hereby corrected as shown below:

Column 1, before line 31, insert a new paragraph:

—Several examples of analogous and non-analogous prior art catheters used for injection of contrast liquid into a heart and/or having holes or openings in a distal end portion are disclosed in the following U.S. and foreign patent publications:

| U.S. Patent No. | Patentee |
| --- | --- |
| 3,938,501 | Erikson |
| 4,531,933 | Norton et al. |
| 4,671,795 | Mulchin |
| 4,694,838 | Wijayarthna et al. |
| 4,735,620 | Ruiz |
| 4,961,731 | Bodicky et al. |
| 4,986,814 | Burney et al. |
| 5,163,431 | Griep |
| 5,201,723 | Quinn |
| 5,221,253 | Coll |

Foreign Patent Publications:

| | |
| --- | --- |
| EP No. 0 129 634 | Drettner |
| EP No. 0 154 403 | Newman and Wijayarathna |
| EP No. 0 453 008 A1 | Griep |
| UK No. 2 166 958 A | Mulchin |

UNITED STATES PATENT AND TRADEMARK OFFICE
CERTIFICATE OF CORRECTION

PATENT NO. : 5,480,392
DATED : January 2, 1996
INVENTOR(S) : Frans Mous

It is certified that error appears in the above-indentified patent and that said Letters Patent is hereby corrected as shown below:

Column 1, line 32, "described in the preamble such" should be --described above--.

Column 1, line 34, "an" should be --the--.

Column 1, lines 34-35, "catheter, as characterized in claim 1" should be --catheter described hereinafter--.

Column 1, line 51, "The invention" should be --The catheter of the invention--.

Column 2, line 21, before "DESCRIPTION" insert --BRIEF--.

Column 2, line 32, before line 32 insert --DESCRIPTION OF THE PREFERRED EMBODIMENT(S)--.

Column 4, line 6, "in side" should be --in said side--.

Column 4, line 31, insert --a-- before "main portion".

Column 4, line 34, insert --a-- before "permanent".

UNITED STATES PATENT AND TRADEMARK OFFICE
CERTIFICATE OF CORRECTION

PATENT NO. : 5,480,392
DATED : January 2, 1996
INVENTOR(S) : Frans Mous

It is certified that error appears in the above-indentified patent and that said Letters Patent is hereby corrected as shown below:

Column 4, line 36, "portion at" should be —-portion, at—-.

Signed and Sealed this

Fourth Day of June, 1996

Attest:

BRUCE LEHMAN

*Attesting Officer*  *Commissioner of Patents and Trademarks*